United States Patent [19]

Chupp

[11] Patent Number: 4,731,109

[45] Date of Patent: Mar. 15, 1988

[54] HERBICIDAL 2-HALOACETANILIDES

[75] Inventor: John P. Chupp, Kirkwood, Mo.

[73] Assignee: Monsanto Company, St. Louis, Mo.

[21] Appl. No.: 358,967

[22] Filed: Mar. 17, 1982

Related U.S. Application Data

[63] Continuation-in-part of Ser. No. 333,345, Dec. 22, 1981, abandoned, and a continuation of Ser. No. 133,718, Mar. 25, 1980, abandoned.

[51] Int. Cl.$^4$ .................... A01N 37/22; C07C 103/32
[52] U.S. Cl. ...................................... 71/118; 564/214
[58] Field of Search .......................... 71/118; 564/214

[56] References Cited

U.S. PATENT DOCUMENTS

| | | | |
|---|---|---|---|
| 3,407,056 | 12/1968 | Schwartz | 71/118 |
| 3,547,620 | 12/1970 | Olin | 71/118 |
| 3,773,492 | 11/1973 | Fischer | 71/92 |
| 3,966,811 | 6/1976 | Krenzer | 206/562 B |
| 4,070,389 | 1/1978 | Martin | 260/465 E |
| 4,137,070 | 1/1979 | Pallos | 71/100 |
| 4,152,137 | 5/1979 | Martin | 71/105 |
| 4,258,196 | 3/1981 | Chupp et al. | 548/165 |

FOREIGN PATENT DOCUMENTS

| | | |
|---|---|---|
| 810763 | 6/1974 | Belgium . |
| 2402983 | 8/1974 | Fed. Rep. of Germany . |
| 2828265 | 1/1980 | Fed. Rep. of Germany . |
| 740767 | 8/1974 | South Africa . |
| 579348 | 7/1976 | Switzerland . |
| 585191 | 1/1977 | Switzerland . |
| 2013188 | 8/1979 | United Kingdom . |

*Primary Examiner*—Catherine L. Mills
*Attorney, Agent, or Firm*—William I. Andress

[57] ABSTRACT

The disclosure herein relates to a group of N-hydrocarbyloxymethyl-2-haloacetanilide compounds, herbicidal compositions containing said compounds as the active ingredient and herbicidal method of use in various crops, particularly, corn and soybeans and other crops including cotton, peanuts, rape and bush beans. The herbicides herein are particularly effective against hard-to-kill perennial weeds such as quackgrass and nutsedges and are also effective against annual weeds.

4 Claims, No Drawings

HERBICIDAL 2-HALOACETANILIDES

RELATED APPLICATION

This is a continuation-in-part application of application Ser. No. 333,345 filed Dec. 22, 1981 now abandoned, which is a continuation of application Ser. No. 133,718, filed Mar. 25, 1980, now abandoned.

BACKGROUND OF THE INVENTION

1. Field of the Invention

This invention pertains to the field of 2-haloacetanilides and their use in the agronomic arts, e.g., as herbicides.

2. Description of the Prior Art

The prior art includes numerous disclosures of 2-haloacetanilides which may be unsubstituted or substituted with a wide variety of substituents on the anilide nitrogen atom and/or on the anilide ring including alkyl, alkoxy, alkoxyalkyl, haloalkyl, halogen, etc., radicals.

Swiss Pat. Nos. 579,348, 585,191 and counterpart Belgian Pat. No. 810,763 contain generic disclosures of N-alkoxyalkyl (wherein the alkyl moiety contains no less than two carbon atoms) -2-chloroacetanilides which may be substituted on the anilide ring at the ortho and meta positions with one or more radicals selected from a plurality of radicals including halogen, alkyl, alkoxy or trifluoromethyl (—$CF_3$). In more particular, the list of compounds in Table I of the Swiss Patents (Table II of the Belgian Patent) includes species substituted with a —$CF_3$ radical in one ortho position with no substituent in the other ortho position (Compound Numbers 37–48) and compounds having —$CF_3$ substitution in a meta position with one ortho position unsubstituted and the other ortho position substituted with a methoxy radical (Compound Numbers 22–25) or a chlorine atom (Compound Numbers 33–36). In addition, the list includes species with a —$CF_3$ radical in one ortho position and a —$CH_3$ in the other ortho position (Compound Numbers 54–56). The compounds in these patents, however, are characterized by an alkoxyalkyl group substituted on the anilide nitrogen atom wherein the alkylene moiety must have no less than two carbon atoms between the nitrogen atom and the oxygen atom of the alkoxy moiety. In contrast, the compounds of this invention are characterized, in part, by the substitution on the anilide nitrogen atom with an alkoxymethyl radical.

The invention compounds have specified combinations of hydrocarbyloxymethyl radicals on the anilide nitrogen, a trifluoromethyl radical in one ortho position and methyl radical, an ethyl radical or hydrogen in the other ortho position. The significance of the differences between compounds of the above patents and compounds of this invention is shown by comparative herbicidal data herein.

U.S. Pat. Nos. 4,070,389, 4,137,070, 4,152,137, and Belgian Pat. No. 862,413 typify the use of very broad generic formulas that can include a huge number of components. These generic formulas can each include haloacetanilides that may be constructed by selection among the great many options available to contain one or more —$CF_3$ and/or ring substituents, and/or nitrogen substituents. The specific compounds which are named in these patents, however, demonstrate that —$CF_3$ was not a preferred substituent, particularly when the N-substituent was an alkoxyalkyl radical. On the contrary, it was virtually ignored. Despite the many compounds named in these patents, only one —$CF_3$ containing haloacetanilide, viz., (2'-trifluoromethyl-α,α-di-chloroacetanilide) is identified (U.S. Pat. No. 4,137,070) and even that compound is not a monochloroacetanilide.

Although an additional substantial body of art relating to a variety of acetanilides exists, very few haloacetanilides of any kind were named which contained a —$CF_3$ and these were almost always in the meta or para position. There is, of course, a very large body of prior art which is directed to haloacetanilides which makes no reference whatever to any —$CF_3$ group.

Research continues in a never-ending effort to identify desirable herbicides. Herbicide properties which, inter alia, are the focus of research and development efforts include an ability to control or suppress a variety of weeds, an ability to provide reasonable crop safety at application rates, longevity under normal weather conditions, an ability to function in a plurality of soils, and an ability to be used in more than one application mode.

It is an object of this invention to provide herbicides which have good activity against a plurality of weeds.

It is a further object of this invention to provide herbicides which provide good crop safety, particularly in corn and soybeans.

It is another object of this invention to provide herbicides which may be used in a variety of soils.

It is still another object of this invention to provide herbicides which exhibit weed suppression over extended periods of time.

It is yet another object of this invention to provide herbicides which are non-toxic and do not require special handling procedures.

It is a still further object of this invention to provide herbicides which are capable of being used in a variety of application modes.

The above and other objects of the invention will become more apparent from the detailed description below.

SUMMARY OF THE INVENTION

The present invention relates to herbicidally active compounds, herbicidal compositions containing these compounds as active ingredients and herbicidal method of use of said compositions in particular crops.

It has now been found that a selective group of 2-haloacetanilides characterized by specific combinations of specific hydrocarbyloxymethyl radicals on the anilide nitrogen atom, a trifluoromethyl (—$CF_3$) radical in one ortho position and a methyl or ethyl radical or hydrogen atom in the other ortho position possess unexpectedly superior and outstanding herbicidal properties.

An important feature of the herbicides of the present invention is their ability to safely control or suppress hard to control weeds in a number of crops. In particular, the herbicides of the present invention safely control or suppress yellow nutsedge, quackgrass, and barnyardgrass in corn and soybeans. In addition individual herbicides have been shown to be effective for other weeds. Control or suppression has been shown for weeds such as lambsquarters, purple nutsedge, smartweed, pigweed, seedling johnsongrass, prickly sida, hemp sesbania, alexandergrass, Texas panicum, wild proso millet, red rice, itchgrass and shattercane, and other noxious weeds such as fall panicum, foxtails, barnyardgrass, crabgrass, etc. Weed stand reduction has also been observed in resistant weeds such as ragweed, velvetleaf, morningglory, cocklebur and purslane. Crops in which individual herbicides may be used safely include cotton, peranuts, rape and snap beans, as well as corn and soybeans.

The compounds of this invention are characterized by the formula

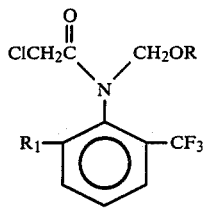

wherein
R is $C_{2-4}$ alkyl, allyl or propargyl and
$R_1$ is hydrogen, methyl or ethyl; provided than
When $R_1$ is hydrogen, R is isopropyl,
when $R_1$ is ethyl, R is ethyl or n-propyl, and
when $R_1$ is methyl, R is ethyl, n-propyl, isopropyl, isobutyl, sec-butyl, allyl or propargyl.

Individual species of this invention are as follows:
N-(ethoxymethyl)-2'-trifluoromethyl-6'-methyl-2-chloroacetanilide.
N-(n-propxoymethyl)-2'-trifluoromethyl-6'-methyl-2-chloroacetanilide.
N-(isopropoxymethyl)-2-trifluoromethyl-6'-methyl-2-chloroacetanilide.
N-(isobutoxymethyl)-2'-trifluoromethyl-6'-methyl-2-chloroacetanilide.
N-(sec-butoxymethyl)-2'-trifluoromethyl-6'-methyl-2-chloroacetanilide.
N-(allyloxymethyl)-2'-trifluoromethyl-6'-methyl-2-chloroacetanilide.
N-(propargyloxymethyl)-2'-trifluoromethyl-6'-methyl-2-chloroacetanilide.
N-(ethoxymethyl)-2'-trifluoromethyl-6'-ethyl-2-chloroacetanilide.
N-(n-propoxymethyl)-2'-trifluoromethyl-6'-ethyl-2-chloroacetanilide.
N-(isoprropoxymethyl)-2'-trifluoromethyl-2-chloroacetanilide.

The utility of the compounds of this invention as the active ingredient in herbicidal compositions formulated therewith and the method of use thereof will be described below.

DETAILED DESCRIPTION OF THE INVENTION

The compounds of this invention may be made by the N-alkylation of the anion of the appropriate secondary 2-haloacetanilide with an alkylating agent under basic conditions. The N-alkylation process is described in more detail in U.S. Pat. No. 4,258,196, assigned to the same assignee herein and in Example 1 herein. Modification of said N-alkylation process involves the in-situ preparation of halomethyl alkyl ethers used as starting materials in said N-alkylation process and is described in Example 1A. The modified N-alkylation process is described in more detaill in U.S. Pat. No. 4,284,564, also assigned to the assignee of this application. The inventions in said U.S. Pat. No. 4,258,196 and U.S. Pat. No. 4,284,564 include the inventor herein and other employees of the assignee herein.

EXAMPLE 1

This example describes the preparation of N-(ethoxymethyl)-2'-trifluoromethyl-6'-methyl-2-chloroacetanilide.

2'-Trifluoromethyl-6'-methyl-2-chloroacetanilide, 4.02 gm (0.016 mol), chloromethyl ethyl ether, 3.02 gm (0.032 mol) and benzyl triethylammonium bromide, 2.0 g, (phase transfer catalyst) were mixed in 75 ml of methylene chloride in a 500 ml round bottom flask equipped with mechanical stirrer and thermometer. Sodium hydroxide (50%), 15 ml, were added all at once with vigorous stirring giving rise to an exotherm to 26° C. After about 5 minutes gas chromatography indicated that the reaction was complete. After 15 minutes, ice and water were added, the layers separated and the organic layer washed with 2.5% sodium chloride, dried, filtered and stripped. The dark-colored residue was distilled on a Kugelrohr and 3.4 g of a yellow oil fraction boiling at 110°–115° C. at 0.1 mm collected. This fraction was taken up in cyclohexane and purified by HPLC using 20% ethyl acetate in cyclohexane. Further distillation of peak fraction by Kugelrohr yielded 3.2 gm (65% yield) of colorless oil, b.p. 100°–110° C. at 0.1 mm Hg; on standing a white solid, m.p. 41°–43° C. crystallized out.

| Anal. for $C_{13}H_{15}ClF_3NO_2$ (%) | | |
| --- | --- | --- |
| Element | Theory | Found |
| C | 50.41 | 50.02 |
| H | 4.88 | 4.81 |
| N | 4.52 | 4.38 |

EXAMPLE 1A

This example illustrates the use of an improved alternative process by which the compounds of this invention may be prepared. A feature of the process of this example is the in-situ formation of the alkylating agent, thus effecting a more efficient, economical and simple operation.

To 83.8 gm of a solution of methylene chloride containing 25.1 g (0.1 mole) of 2-trifluoromethyl-6-methyl-2-chloroacetanilide was added 5.8 g (0.1925 mole) of powdered para formaldehyde and 8.9 g (0.1925 mole) of absolute ethanol. The slurry was cooled to 10° C. and stirred while 10.6 g (0.5775 mole) of HCl was bubbled in over a period of 30 minutes. The resulting two phase solution was purged with nitrogen for 15 minutes at 0° C. To this mixture was added 1.35 g (5.37 wt % of the starting sec-anilide) of benzyltriethylammonium chloride as phase transfer catalyst. The above chilled, 2-phase solution was added dropwise to a chilled, rapidly stirred mixture of 60 g of 50% NaOH, 60 g of $H_2O$, 35 g of methylene chloride and 0.3 g of phase transfer catalyst over a 15 minute period. After stirring for an additional 5 minutes, 120 g of water was added and the layers separated. The organic layer was washed successively with 30 and 100 ml portions of 10% HCl. Area % Glc indicated 86% of N-(ethoxymethyl)-2'-trifluoromethyl-6'-methyl-2-chloroacetanilide and 10.7% of unreacted sec-amide. The above reaction was repeated exactly, except only 0.9 g of phase transfer catalyst is used in the sec-anailide/tertiaryanilide mixture. After separating the caustic and organic layers, the organic layer was washed with 80 ml of 10% HCl and stripped to give 31.5 gm of red oil. To this oil was added 12 g of H$_2$O and the mixture again stripped under aspirator vacuum. The resulting oil was finally stripped at 0.2 mm Hg, 60° C. to leave 29.3 gm (94.7% yield). This material is 95.0 wt % assay of N-(ethoxymethyl)-2'-trifluoromethyl-6'-methyl-2-chloroacetanilide. 96.3 area % assay.

EXAMPLES 2-10

Following substantially the same procedures, quantities of reactants and general reaction conditions as described in Examples 1 or 1A, but substituting the appropriate starting sec-anilide and alkylating agent to obtain the end product, other compounds according to the above formula are prepared; these compounds are identified in Table I.

| Anal. for C$_{11}$H$_{11}$ClF$_3$NO (%) | | |
|---|---|---|
| Element | Theory | Found |
| C | 49.73 | 49.35 |
| H | 4.17 | 4.09 |
| N | 5.27 | 5.38 |

The product was identified as 2'-trifluoromethyl-6'-ethyl-2-chloroacetanilide.

Primary amines of the type used to prepare secondary anilides by haloacetylation as described above are known in the literature; see, e.g., the above-mentioned Swiss Pat. Nos. 579,348 and 585,191, U.S. Pat. No. 3,966,811 and British Application No. 2,013,188, and may be prepared by processes disclosed in the prior art as indicated below.

TABLE I

| Example No. | Compound | Empirical Formula | B.P. °C. (mm Hg.) | Element | Analysis Calculated | Found |
|---|---|---|---|---|---|---|
| 2 | N—(isopropoxymethyl)-2'-trifluoromethyl-2-chloroacetanilide | C$_{13}$H$_{15}$F$_3$ClNO$_2$ | 100–101 (0.05) | C<br>H<br>N | 50.41<br>4.88<br>4.52 | 50.52<br>4.89<br>4.46 |
| 3 | N—(n-propoxymethyl)-2'-trifluoromethyl-6'-methyl-2-chloroacetanilide | C$_{14}$H$_{17}$ClF$_3$NO$_2$ | 110–120° C. (0.1) | C<br>H<br>N | 51.94<br>5.29<br>4.33 | 51.80<br>5.17<br>4.28 |
| 4 | N—(isopropoxymethyl)-2'-trifluoromethyl-6'-methyl-2-chloroacetanilide | C$_{14}$H$_{17}$ClF$_3$NO$_2$ | 110–120° C. (0.1) | C<br>H<br>N | 51.94<br>5.29<br>4.33 | 51.69<br>5.23<br>4.22 |
| 5 | N—(isobutoxymethyl)-2'-trifluoromethyl-6'-methyl-2-chloroacetanilide | C$_{15}$H$_{19}$ClF$_3$NO$_2$ | 130–140° C. (0.1) | C<br>H<br>N | 53.34<br>5.67<br>4.15 | 53.07<br>5.61<br>4.01 |
| 6 | N—(sec-butoxymethyl)-2'-trifluoromethyl-6'-methyl-2-chloroacetanilide | C$_{15}$H$_{19}$ClF$_3$NO$_2$ | 135–142° C. (0.05) | C<br>H<br>N | 53.34<br>5.67<br>4.15 | 53.23<br>5.67<br>4.13 |
| 7 | N—(allyloxymethyl)-2'-trifluoromethyl-6'-methyl-2-chloroacetanilide | C$_{14}$H$_{15}$ClF$_3$NO$_2$ | 123–125° C. (0.1) | C<br>H<br>N | 52.27<br>4.70<br>4.35 | 52.11<br>4.74<br>4.34 |
| 8 | N—(propargyloxymethyl)-2'-trifluoromethyl-6'-methyl-2-chloroacetanilide | C$_{14}$H$_{13}$ClF$_3$NO$_2$ | Oil | C<br>H<br>N | 52.59<br>4.10<br>4.38 | 52.44<br>4.14<br>4.34 |
| 9 | N—(ethoxymethyl)-2'-trifluoromethyl-6'-ethyl-2-chloroacetanilide | C$_{14}$H$_{17}$ClF$_3$NO$_2$ | 133–135° C. (0.02) | C<br>H<br>N | 51.94<br>5.29<br>4.33 | 51.32<br>5.26<br>4.39 |
| 10 | N—(n-propoxymethyl)-2'-trifluoromethyl-6'-ethyl-2-chloroacetanilide | C$_{15}$H$_{19}$ClF$_3$NO$_2$ | Colorless Oil | C<br>H<br>N | 53.34<br>5.67<br>4.15 | 53.74<br>5.77<br>4.16 |

The secondary anilide starting materials used in the above examples to prepare the compounds of this invention are suitably prepared by conventional chloroacetylation of the appropriate primary amine as exemplified in Example 11 below.

EXAMPLE 11

This example illustrates the preparation of the secondary anilide starting material used to prepare a species of the compound of this example, i.e., the compound of Example 9.

2-Trifluoromethyl-6-ethylaniline, 6.0 gm (0.03174 mol) was dissolved in 75 ml of toluene and 3.77 gm (0.033 mol) of chloroacetyl chloride added cautiously. The resulting slurry was raised to reflux temperature and held for 4 hours. Thereafter, the mixture was diluted with an equal volume of hexane and the mixture let stand. The product crystallized and the resulting solid was filtered and air dried to give 5.8 gm (69% yield); the filtrate was stripped to produce another 2.7 gm of white solid, m.p. 121°–124° C. (sealed tube).

Amines such as 2-trifluoromethyl-6-methyl amine may be prepared by reacting commercially available ortho trifluoromethyl aniline with dimethyl sulfide in the presence of a base and an oxidizing agent such as N-chlorosuccinimide to provide a sulfilimine which may be heated or subjected to catalysis to cause sulfilimine rearrangement to an ortho methylthiomethyl aniline. The ortho methylthiomethyl group can then be reduced, for example, with a prior art hydrogenation employing Raney nickel or other caatalysts to form 2-trifluoromethyl-6-methyl aniline. Alternatively, the ortho methylthiomethyl aniline can be oxidized with a peroxide to the corresponding sulfoxide. Such reactions are known in the art and are described, inter alia, in Gassman, Tetrahedron Letters 497 (1972), Gassman, Tetrahedron Letters 24, 2055–2058 (1977), Vilsmeier, Tetrahedron Letters 624 (1972), Jackson U.S. Pat. Nos. 3,966,371 and 4,006,183, and Claus, Mh Chem. Bd. 102, pp. 1571–1582 (1971). In a variation of the sulfilimine reaction, when a base such as sodium hydroxide is used, the neutralization can be accompanied by a conversion of by-product succinimide to an aqueous solution of sodium succinimide which can be regenerated to N-chlorosuccinimide. The sulfoxide can be converted to a methyl group by electrolysis, as described in corresponding application, Ser. No. 358,771, filed of even date herewith. In another method, the 2-trifluoromethyl-6-methylthiomethyl aniline can be converted to the corresponding sulfoxide by anhydrous reaction with chlorine followed by hydrolysis, and the resulting 2-methyl-sulfinylmethyl-6-trifluoromethyl aniline reacted with HCl to provide 2-chloromethyl-6-trifluoromethyl anilinium chloride, which can be converted to 2-trifluoromethyl-6-methyl aniline by hydrogenation as disclosed in copending application Ser. No. 358,772 filed concurrently herewith. Another mode of preparing 2-trifluoromethyl-6-methyl aniline involves reacting 2-chloromethyl-6-trifluoromethyl aniline (prepared by neutralizing said ammonium salt thereof) with trimethylamine to form the corresponding quaternary trimethylammonium chloride salt, which is then hydrogenated in water or an aqueous alcohol. e.g., methanol, solvent in the presence of a hydrogenation catalyst e.g., palladium on charcoal.

2-trifluoromethyl-6-ethyl aniline can be prepared, for example, in the manner generally described by Fuhner, et al, J. Org. Chem., 44, No. 7, pp. 1133–1136 (1979), by first reacting 2-trifluoromethyl aniline with pivaloyl chloride in an inert solvent containing a catalyst, e.g., dimethyl formamide; reacting the formed N-pivaloyl-2-trifluoromethyl aniline with n-butyl lithium, then alkylating with ethyl iodide and finally the pivalanilide hydrolyzed in strong acid and recovering the product, 2-ethyl-6-trifluoromethyl aniline. Alternatively, 2-trifluoromethyl-6-methylthiomethyl aniline can be oxidized with peracetic acid to 2-trifluoromethyl-6-methylsulfonylmethyl nitrobenzene, followed by reaction with an alkylating agent, e.g., dimethyl sulfate in the presence of sodium hydroxide, and a phase transfer catalyst in an organic solvent to obtain 6-trifluoromethyl-2-(1-methylsulfonylethyl)nitrobenzene, and the nitro group reduced to the corresponding aniline by hydrogenation in the presence of a hydrogenation catalyst; then finally reductively desulfurized, preferably by electrolysis to the 2-ethyl-6-trifluoromethyl aniline. Such process is disclosed in copending application Ser. No. 358,774, filed concurrently herewith.

As noted above, the compounds of this invention have been found to be effective as herbicides, particularly as pre-emergence herbicides, although post-emergence activity has also been shown. The pre-emergence tests referred to herein include both greenhouse and field tests. In the greenhouse tests, the herbicide is applied either as a surface application after planting the seeds or vegetative propagules or by incorporation into a quantity of soil to be applied as a cover layer over the test seeds in pre-seeded test containers. In the field tests, the herbicide may be applied pre-plant incorporation ("P.P.I") into the soil, i.e., the herbicide is applied to the surface of the soil, then incorporated therein by mixing means followed by planting of the crop seeds, or the herbicide may be applied to the surface ("S.A.", surface application) after the crop seed is planted.

The surface application ("S.A.") test method used in the greenhouse is performed as follows: Containers, e.g., aluminum pans typically 9.5"×5.25"×2.75" (24.13 cm×13.34 cm×6.99 cm) or plastic pots 3.75"×3.75"×3" (9.53 cm×9.53 cm×7.62 cm) having drain holes in the bottom, are level-filled with Ray silt loam soil then compacted to a level 0.5 inch (1.27 cm) from the top of the pots. The pots are then seeded with plant species to be tested, covered with a 0.5 inch layer of the test soils. The herbicide is then applied to the surface of the soil, e.g., with a belt sprayer at 20 gal/A, 30 psi (187 l/ha, 2.11 kg/cm²). Each pot receives 0.25 inch (0.64 cm) water as overhead irrigation and the pots are then placed on greenhouse benches for subsequent sub-irrigation as needed. As an alternative procedure, the overhead irrigation may be omitted. Observations of herbicidal effects are made about three weeks after treatment.

The herbicide treatment by soil incorporation ("S.I.") used in the greenhouse tests are as follows:

A good grade of top soil is placed in aluminum pans and compacted to a depth of three-eighths to one-half inch from the top of the pan. On the top of the soil is placed a number of seeds or vegetative propagules of various plant species. The soil required to level fill the pans after seeding or adding vegetative propagules is weighed into a pan. The soil and a known amount of the active ingredient applied in a solvent or as a wettable powder suspension are thoroughly mixed, and used to cover the prepared pans. After treatment, the pans are given an initial overhead irrigation of eater, equivalent to one-fourth inch (0.64 cm) rainfall, then watered by subirrigation as need to give adequate moisture for germination and growth. As an alternative procedure, the overhead irrigation may be omitted. Observations are made about 2–3 weeks after seeding and treatment.

Tables II and III summarize results of tests conducted to determine the pre-emergence herbicidal activity of the compounds of this invention; in these tests, the herbicides were applied by soil incorporation and sub-irrigation watering only. The herbicidal rating was obtained by means of a fixed scale based on the percent injury of each plant species. The ratings are defined as follows:

| % Control | Rating |
| --- | --- |
| 0–24 | 0 |
| 25–49 | 1 |
| 50–74 | 2 |
| 75–100 | 3 |
| Undetermined | 5 |

The plant species utilized in one set of tests, the data for which are shown in Table II, are identified by letter in accordance with the following legend:

| | | |
| --- | --- | --- |
| A Canada Thistle | E Lambsquarters | I Johnsongrass |
| B Cocklebur | F Smartweed | J Downy Brome |
| C Velvetleaf | G Yellow Nutsedge | K Barnyardgrass |
| D Morningglory | H Quackgrass | |

TABLE II

Pre-Emergent

| Compound of Example No. | kg/h | A | B | C | D | E | F | G | H | I | J | K |
| --- | --- | --- | --- | --- | --- | --- | --- | --- | --- | --- | --- | --- |
| 1 | 11.2 | 5 | 3 | 3 | 3 | 3 | 3 | 3 | 3 | 3 | 3 | 3 |
|   | 5.6 | 5 | 2 | 2 | 3 | 3 | 3 | 3 | 3 | 3 | 3 | 3 |
| 2 | 11.2 | 3 | 1 | 2 | 3 | 3 | 3 | 3 | 3 | 2 | 3 | 3 |
|   | 5.6 | 2 | 0 | 2 | 3 | 3 | 2 | 3 | 3 | 1 | 3 | 3 |
| 3 | 11.2 | 5 | 3 | 2 | 3 | 3 | 3 | 3 | 3 | 3 | 3 | 3 |
|   | 5.6 | 5 | 2 | 1 | 2 | 3 | 3 | 3 | 3 | 3 | 3 | 3 |
| 4 | 11.2 | 5 | 3 | 2 | 3 | 3 | 3 | 3 | 3 | 3 | 3 | 3 |
|   | 5.6 | 5 | 0 | 0 | 3 | 3 | 3 | 3 | 3 | 1 | 3 | 3 |
| 5 | 11.2 | 5 | 2 | 1 | 3 | 3 | 3 | 3 | 3 | 3 | 3 | 3 |
|   | 5.6 | 5 | 2 | 0 | 1 | 3 | 3 | 3 | 3 | 3 | 3 | 3 |
| 6 | 11.2 | 3 | 2 | 2 | 3 | 3 | 3 | 3 | 3 | 3 | 3 | 3 |

TABLE II-continued

| Compound of Example No. | kg/h | Pre-Emergent Plant Species | | | | | | | | | | |
|---|---|---|---|---|---|---|---|---|---|---|---|---|
| | | A | B | C | D | E | F | G | H | I | J | K |
| | 5.6 | 3 | 2 | 1 | 2 | 3 | 3 | 3 | 3 | 1 | 3 | 3 |
| 7 | 11.2 | 3 | 2 | 1 | 3 | 3 | 3 | 3 | 3 | 3 | 3 | 3 |
| | 5.6 | 3 | 1 | 1 | 2 | 3 | 3 | 3 | 3 | 0 | 3 | 3 |
| 8 | 11.2 | 3 | 1 | 1 | 3 | 3 | 3 | 3 | 3 | 0 | 3 | 3 |
| | 5.6 | 3 | 1 | 1 | 2 | 3 | 3 | 1 | 3 | 1 | 3 | 3 |
| 9 | 11.2 | 3 | 2 | 2 | 3 | 3 | 3 | 3 | 3 | 3 | 3 | 3 |
| | 5.6 | 3 | 2 | 2 | 3 | 3 | 3 | 3 | 3 | 2 | 3 | 3 |
| 10 | 11.2 | 3 | 0 | 2 | 3 | 3 | 3 | 3 | 3 | 3 | 3 | 3 |
| | 5.6 | 3 | 0 | 1 | 2 | 3 | 2 | 3 | 3 | 2 | 3 | 3 |

The compounds were further tested by utilizing the above procedure on the following plant species:

| L Soybean | R Hemp Sesbania |
|---|---|
| M Sugarbeet | E Lambsquarters |
| N Wheat | F Smartweed |
| O Rice | C Velvetleaf |
| P Sorghum | J Downy brome |
| B Cocklebur | S Panicum Spp. |
| Q Wild Buckwheat | K Barnyardgrass |
| D Morningglory | T Crabgrass |

The results are summarized in Table III.

TABLE III

| Compound of Example No. | kg/h | Pre-Emergent | | | | | | | | | | | | | | | |
|---|---|---|---|---|---|---|---|---|---|---|---|---|---|---|---|---|
| | | L | M | N | O | P | B | Q | D | R | E | F | C | J | S | K | T |
| 1 | 5.6 | 1 | 2 | 3 | 3 | 3 | 0 | 3 | 3 | 3 | 3 | 3 | 2 | 3 | 3 | 3 | 3 |
| | 1.12 | 0 | 1 | 1 | 2 | 3 | 0 | 1 | 2 | 2 | 3 | 2 | 0 | 3 | 3 | 3 | 3 |
| | 0.28 | 0 | 1 | 0 | 2 | 1 | 0 | 1 | 0 | 3 | 3 | 3 | 0 | 2 | 3 | 3 | 3 |
| | 0.056 | 0 | 0 | 0 | 0 | 0 | 0 | 0 | 0 | 1 | 1 | 1 | 0 | 0 | 2 | 2 | 3 |
| | 0.0112 | 0 | 0 | 0 | 0 | 0 | 0 | 0 | 0 | 0 | 1 | 1 | 0 | 0 | 1 | 2 | 2 |
| 2 | 5.6 | 0 | 3 | 3 | 3 | 3 | 1 | 3 | 3 | 3 | 3 | 3 | 1 | 3 | 3 | 3 | 3 |
| | 1.12 | 0 | 1 | 1 | 3 | 3 | 1 | 0 | 3 | 1 | 3 | 0 | 0 | 3 | 3 | 3 | 3 |
| | 0.28 | 0 | 0 | 0 | 2 | 2 | 0 | 0 | 0 | 0 | 3 | 0 | 0 | 1 | 3 | 3 | 3 |
| | 0.056 | 0 | 0 | 0 | 1 | 0 | 0 | 0 | 0 | 0 | 2 | 3 | 0 | 0 | 3 | 3 | 3 |
| | 0.0112 | 0 | 0 | 0 | 0 | 0 | 0 | 0 | 0 | 0 | 1 | 0 | 0 | 0 | 3 | 3 | 3 |
| | 0.0056 | 0 | 0 | 0 | 0 | 0 | 0 | 0 | 0 | 0 | 3 | 0 | 0 | 0 | 1 | 0 | 1 |
| 3 | 5.6 | 2 | 3 | 3 | 3 | 3 | 2 | 3 | 3 | 3 | 3 | 3 | 1 | 3 | 3 | 3 | 3 |
| | 1.12 | 1 | 3 | 2 | 3 | 3 | 1 | 3 | 2 | 3 | 3 | 3 | 1 | 3 | 3 | 3 | 3 |
| | 0.28 | 0 | 1 | 2 | 2 | 1 | 0 | 1 | 0 | 1 | 3 | 3 | 0 | 2 | 3 | 3 | 3 |
| | 0.056 | 0 | 1 | 1 | 1 | 2 | 2 | 1 | 0 | 2 | 1 | 1 | 0 | 0 | 2 | 2 | 3 |
| | 0.0112 | 0 | 1 | 0 | 0 | 0 | 0 | 0 | 0 | 1 | 0 | 0 | 0 | 0 | 3 | 3 | 3 |
| 4 | 5.6 | 1 | 2 | 3 | 3 | 3 | 1 | 3 | 3 | 3 | 3 | 3 | 1 | 3 | 3 | 3 | 3 |
| | 1.12 | 0 | 2 | 2 | 3 | 3 | 0 | 2 | 0 | 2 | 3 | 3 | 0 | 3 | 3 | 3 | 3 |
| | 0.28 | 0 | 2 | 1 | 3 | 3 | 2 | 2 | 3 | 2 | 3 | 3 | 0 | 3 | 3 | 3 | 3 |
| | 0.056 | 0 | 1 | 0 | 1 | 2 | 1 | 2 | 0 | 1 | 3 | 1 | 0 | 2 | 3 | 3 | 3 |
| | 0.0112 | 0 | 1 | 0 | 0 | 0 | 1 | 1 | 0 | 0 | 3 | 1 | 0 | 1 | 2 | 3 | 3 |
| 5 | 5.6 | 1 | 3 | 3 | 3 | 3 | 2 | 3 | 3 | 3 | 3 | 3 | 1 | 3 | 3 | 3 | 3 |
| | 1.12 | 0 | 1 | 0 | 3 | 3 | 1 | 3 | 3 | 1 | 3 | 3 | 0 | 3 | 3 | 3 | 3 |
| | 0.28 | 0 | 2 | 0 | 2 | 2 | 2 | 2 | 1 | 3 | 3 | 3 | 0 | 3 | 3 | 3 | 3 |
| | 0.056 | 0 | 2 | 0 | 1 | 2 | 1 | 2 | 2 | 2 | 3 | 1 | 0 | 2 | 3 | 3 | 3 |
| | 0.0112 | 0 | 2 | 0 | 1 | 0 | 2 | 2 | 2 | 2 | 3 | 1 | 0 | 1 | 1 | 3 | 3 |
| 6 | 5.6 | 2 | 2 | 3 | 3 | 3 | 2 | 3 | 3 | 3 | 2 | 3 | 1 | 3 | 3 | 3 | 3 |
| | 1.12 | 1 | 2 | 3 | 3 | 1 | 1 | 3 | 1 | 2 | 2 | 2 | 0 | 3 | 3 | 3 | 3 |
| | 0.28 | 1 | 2 | 2 | 3 | 2 | 0 | 1 | 1 | 2 | 1 | 1 | 0 | 3 | 3 | 3 | 3 |
| | 0.056 | 0 | 0 | 0 | 0 | 0 | 0 | 0 | 0 | 0 | 2 | 1 | 0 | 2 | 3 | 3 | 3 |
| | 0.0112 | 0 | 0 | 0 | 0 | 0 | 0 | 0 | 0 | 0 | 0 | 0 | 0 | 0 | 0 | 3 | 3 |
| 7 | 5.6 | 3 | 3 | 3 | 3 | 3 | 2 | 3 | 3 | 3 | 3 | 3 | 0 | 3 | 3 | 3 | 3 |
| | 1.12 | 1 | 2 | 3 | 3 | 3 | 0 | 3 | 3 | 2 | 2 | 3 | 0 | 3 | 3 | 3 | 3 |
| | 0.28 | 0 | 2 | 2 | 2 | 2 | 0 | 1 | 0 | 2 | 3 | 2 | 0 | 3 | 3 | 3 | 3 |
| | 0.056 | 0 | 1 | 0 | 1 | 0 | 0 | 0 | 0 | 1 | 0 | 0 | 0 | 0 | 3 | 3 | 3 |
| | 0.0112 | 0 | 0 | 0 | 0 | 0 | 0 | 0 | 0 | 0 | 0 | 0 | 0 | 0 | 1 | 2 | 3 |
| 8 | 5.6 | 0 | 3 | 3 | 3 | 3 | 1 | 3 | 3 | 3 | 3 | 3 | 1 | 3 | 3 | 3 | 5 |
| | 1.12 | 0 | 3 | 1 | 3 | 1 | 1 | 1 | 2 | 1 | 2 | 2 | 0 | 3 | 3 | 3 | 5 |
| | 0.28 | 0 | 2 | 1 | 2 | 1 | 0 | 0 | 0 | 1 | 1 | 1 | 0 | 3 | 3 | 3 | 5 |
| | 0.056 | 0 | 1 | 0 | 0 | 0 | 0 | 0 | 5 | 0 | 0 | 0 | 1 | 2 | 3 | 3 | 5 |
| | 0.0112 | 0 | 1 | 0 | 0 | 0 | 0 | 0 | 0 | 0 | 0 | 0 | 0 | 1 | 3 | 3 | 5 |
| 9 | 5.6 | 2 | 3 | 3 | 3 | 3 | 2 | 3 | 3 | 3 | 3 | 3 | 2 | 3 | 3 | 3 | 3 |
| | 1.12 | 1 | 2 | 3 | 3 | 3 | 0 | 2 | 2 | 3 | 2 | 3 | 0 | 3 | 3 | 3 | 3 |
| | 0.28 | 2 | 2 | 3 | 3 | 1 | 0 | 1 | 0 | 3 | 1 | 3 | 0 | 3 | 3 | 3 | 3 |
| | 0.056 | 0 | 1 | 1 | 1 | 0 | 0 | 1 | 0 | 0 | 0 | 0 | 0 | 2 | 3 | 3 | 3 |
| | 0.0112 | 0 | 0 | 0 | 0 | 0 | 0 | 0 | 1 | 5 | 5 | 0 | 0 | 0 | 2 | 2 | 2 |
| 10 | 5.6 | 3 | 3 | 3 | 3 | 3 | 0 | 3 | 3 | 3 | 3 | 2 | 3 | 3 | 3 | 3 | 3 |
| | 1.12 | 0 | 3 | 3 | 3 | 3 | 0 | 2 | 1 | 2 | 2 | 3 | 0 | 3 | 3 | 3 | 3 |
| | 0.28 | 0 | 2 | 2 | 2 | 1 | 0 | 2 | 0 | 1 | 2 | 1 | 0 | 3 | 3 | 3 | 3 |
| | 0.056 | 0 | 1 | 0 | 1 | 0 | 0 | 1 | 0 | 0 | 3 | 0 | 0 | 2 | 3 | 3 | 3 |
| | 0.0112 | 0 | 1 | 1 | 0 | 0 | 0 | 0 | 0 | 0 | 0 | 0 | 0 | 0 | 0 | 2 | 1 |

Selective suppression of weeds with the invention herbicides has been found in a variety of crops including, of particular interest, corn and soybeans. Individual herbicides of the invention also provide crop safety with others such as cotton, peanuts, rape and snapbeans (bush beans).

Certain grass crops, e.g., wheat and sorghum, however, have not generally proven to be particularly tolerant to the herbicides of this invention, as is true with most 2-haloacetanilides. However, safener compounds have been developed and others are continuously being developed with less injury to crops by said herbicides.

In the discussion and tables of data below, reference is made to herbicide application rates symbolized as "$GR_{15}$" and "$GR_{85}$"; these rates are given in kilograms per hectare (kg/ha) which are convertible into pounds per acre (lbs/A) by dividing the kg/ha rate by 1.12. $GR_{15}$ defines the maximum rate of herbicide required to produce 15% or less crop injury, and $GR_{85}$ defines the minimum rate required to achieve 85% inhibition of weeds. The $GR_{15}$ and $GR_{85}$ rates are used as a measure of potential commercial performance, it being understood, of course, that suitable commercial herbicides may exhibit greater or lesser plant injuries within reasonable limits.

A further guide to the effectiveness of a chemical as a selective herbicide is the "selectivity factor" ("SF") for a herbicide in given crops and weeds. The selectivity factor is a measure of the relative degree of crop safety and weed injury and is expressed in terms of the $GR_{15}/GR_{85}$ ratio, i.e., the $GR_{15}$ rate for the crop divided by the $GR_{85}$ rate for the weed, both rates in kg/ha (lb/A). In the tables below, selectivity factors are shown in parenthesis following the $GR_{85}$ rate for each weed; the symbol "NS" indicates "non-selective". Marginal or undetermined selectivity is indicated by a dash (—).

Since crop tolerance and weed control are interrelated, a brief discussion of this relationship in terms of selectivity factors is meaningful. In general, it is desirable that crop safety factors, i.e., herbicide tolerance values, be high, since higher concentrations of herbicide are frequently desired for one reason or another. Conversely, it is desirable that weed control rates be small, i.e., the herbicide possesses high unit activity, for economical and possibly ecological reasons. However, small rates of application of a herbicide may not be adequate to control certain weeds and a larger rate may be required. Hence the best herbicides are those which control the greatest number of weeds with the least amount of herbicide and provide the greatest degree of crop safety, i.e., crop tolerance. Accordingly, use is made of selectivity factors (define above) to quantify the relationship between crop safety and weed control. With reference to the selectivity factors listed in the tables, the higher the numerical value, the greater selectivity of the herbicide for weed control in a given crop.

In order to illustrate the unexpectedly superior properties of the compounds of this invention both on an absolute basis and on a relative basis, comparative tests were conducted in the greenhouse with prior art compounds identified as follows (using the same nomenclature as for the invention compounds):
  A. N-(methoxyethyl)-2'-trifluoromethyl-2-chloroacetanilide.
  B. N-(ethoxyethyl)-2'-trifluoromethyl-2-chloroacetanilide.

In Table IV pre-emergence herbicidal activity data are presented comparing the relative efficacy of the invention compounds and said prior art compounds as selective herbicides against the resistant and troublesome perennial weeds quackgrass and yellow nutsedge in soybeans and corn, respectively. These weeds are commonly associated with such major crops as corn and soybeans. The test data in Table IV were obtained under identical procedural conditions and represent two replicate runs (except for the compound of Example 9 which was present in one comparative test). The test procedure was the same as described for Tables II and III but modified by the application of an initial overhead irrigation equivalent to ¼" (0.64 cm) rainfall; subsequent watering was accomplished by subirrigation. "NS" means non-selective within the test limits.

TABLE IV

| Compound | $GR_{85}$ (Kg/Ha) | | $GR_{15}$ (Kg/Ha) | |
| | Quackgrass | Yellow Nutsedge | Corn | Soybeans |
| --- | --- | --- | --- | --- |
| Replicate #1 | | | | |
| A | 2.5* | — | >2.2 (—) | >2.2 (—) |
| | — | 1.2 | >2.2 (>2) | >2.2 (>2) |
| B | 0.56 | — | 1.2 (2) | 2.0 (3.5) |
| | — | 0.47 | 1.2 (2.5) | 2.0 (4) |
| Ex. 1 | 0.18 | — | 0.76 (4) | 3.1 (17) |
| | — | 0.20 | 0.76 (4) | 3.1 (15) |
| Ex. 2 | 0.26 | — | 3.1 (12) | 1.7 (6.5) |
| | — | 0.17 | 3.1 (18) | 1.7 (10) |
| Ex. 3 | 0.12 | — | 0.78 (6.5) | 1.1 (9) |
| | — | 0.11 | 0.78 (7) | 1.1 (10) |
| Ex. 4 | 0.33 | — | 1.7 (5) | 1.1 (3) |
| | — | 0.28 | 1.7 (6) | 1.1 (4) |
| Replicate #2 | | | | |
| A | >2.2 | — | 2.2 (NS) | >2.2 (—) |
| | — | 1.0 | 2.2 (2) | >2.2 (>2) |
| B | 0.64 | — | 0.37 (NS) | 2.0 (3) |
| | — | 0.43 | 0.37 (NS) | 2.0 (4.5) |
| Ex. 1 | 0.16 | — | 0.76 (5) | 2.2 (14) |
| | — | 0.12 | 0.76 (6) | 2.2 (18) |
| Ex. 2 | 0.22 | — | 0.78 (3.5) | 1.7 (7.5) |
| | — | 0.20 | 0.78 (4) | 1.7 (8.5) |
| Ex. 3 | 0.13 | — | 0.73 (5.5) | 1.1 (8.5) |
| | — | 0.21 | 0.73 (3.5) | 1.1 (5) |
| Ex. 4 | 0.18 | — | 2.0 (11) | 1.7 (9.5) |
| | — | 0.22 | 2.0 (8.5) | 1.7 (7.5) |
| Ex. 9 | 0.20 | — | 2.2 (11) | 2.1 (10.5) |
| | — | 0.17 | 2.2 (13) | 2.1 (12.5) |

*Extrapolated value

Referring to the data in Table IV, it will be noted that every invention compound exhibited from substantially to exceedingly higher selectivity factors (values in parentheses) against both quackgrass and yellow nutsedge than the unit activity and selectivity factors that were determined for compounds of the prior art. In more particular, it is noted that the unit activities (relative phytotoxicity per unit of herbicide) of the invention compounds are markedly higher against quackgrass and yellow nutsedge that those of the prior art compounds, while maintaining crop safety (as reflected in the selectivity factors). Of special note are the outstandingly high selectivity factors of the compounds of Examples 1–4 and 9, particularly in soybeans and Examples 2, 4 and 9 in corn.

Further comparative data showing the relative efficacy of the invention compounds of Example 1 vis-a-vis the prior art compounds of the above mentioned Swiss Pat. Nos. 579,348 and 585,191 against quackgrass and yellow nutsedge in corn and soybeans is presented in Table V. More particularly, the prior art compounds are identified as follows:
  C. N-(methoxyethyl)-2'-trifluoromethyl-6'-methyl-2-chloroacetanilide (compound 54).
  D. N-(methoxyisopropyl)-2'-trifluoromethyl-6'-methyl-2-chloroacetanilide (compound 56).
  E. N-(ethoxyethyl)-2'-trifluoromethyl-6'-methyl-2-chloroacetanilide (compound 55).

TABLE V

| Compound | $GR_{85}$ (Kg/Ha) | | $GR_{15}$ (Kg/Ha) | |
| | Quackgrass | Yellow Nutsedge | Corn | Soybeans |
| --- | --- | --- | --- | --- |
| C | 0.28 | — | 1.3 (5) | >2.8 (>10) |
| | — | 0.28 | 1.3 (5) | >2.8 (>10) |

TABLE V-continued

| Compound | GR$_{85}$ (Kg/Ha) | | GR$_{15}$ (Kg/Ha) | |
|---|---|---|---|---|
| | Quackgrass | Yellow Nutsedge | Corn | Soybeans |
| D | 1.7 | — | 2.0 (1) | >2.8 (>1.5) |
| | — | 0.45 | 2.0 (4) | >2.8 (>6) |
| E | 0.28 | — | 0.67 (2.5) | 0.84 (3) |
| | — | 0.22 | 0.67 (3) | 0.84 (4) |
| Ex. 1 | 0.08 | — | 2.2 (27.5) | 2.8* (35) |
| | — | 0.10 | 2.2 (22) | 2.8* (28) |

*Extrapolated value

Referring to the data in Table V, it will be noted that the compound of Example 1 demonstrated exceedingly higher selectivity factors against both quackgrass and yellow nutsedge in both corn and soybeans than the compounds of the prior art. Again, it is noted that unit activities of the prior art compounds were markedly lower, (i.e., higher GR$_{85}$ rates) against quackgrass and yellow nutsedge than those of the invention compound of Example 1.

From the comparative data shown in Tables IV and V, it will be apparent that the invention compounds exhibited outstandingly higher and unexpectedly superior herbicidal efficacy against the herbicidally resistant perennial weeds quackgrass and yellow nutsedge in two major crops, i.e., soybeans and corn, than the prior art compounds which were included in the same test.

As in the case in agricultural testing generally, the absolute values of data (e.g., application rates for 85% control) can vary from test to test depending on a wide variety of factors, not all of which can be controlled precisely between tests conducted at different times. Importantly, in each of the above tests, even though the absolute values vary to some degree, the invention compounds are outstandingly superior to the prior art compounds that were included in the same test.

Additionally, pre-emergence herbicidal data from other tests have established that compounds according to this invention also selectively suppress quackgrass, yellow nutsedge and/or other weeds in one or more of the crops cotton, peanuts, bush beans and/or rape. For example, in Table VI are presented data showing the herbicidal selectivity of the compounds of Examples 1 and 2 against quackgrass in rape and snap beans. Unless otherwise noted; greenhouse tests in Table VI and in other tables below involved herbicide treatments by soil incorporation and an initial overhead irrigation followed by subirrigation as described above.

TABLE VI

| Compound | GR$_{15}$ Rate (Kg/Ha) | | GR$_{85}$ Rate (Kg/Ha) |
|---|---|---|---|
| | Rape | Snapbeans | Quackgrass |
| Ex. 1 | 0.85 | — | 0.12 (7) |
| | — | 0.90 | 0.12 (7) |
| Ex. 2 | 1.9 | — | 0.28 (7) |
| | — | 2.2 | 0.28 (8) |

The compound of Examples 1 and 2 was also tested in the field to determine its pre-emergence selectivity against foxtail (spp), barnyardgrass, wild proso millet, smartweed, lambsquarters and pigweed in a plurality of crops; the data (representing three replicate runs) are shown in Table VII for both surface application (S.A.) and soil incorporation (PPI, i.e., preplant incorporation) of the herbicide. The seeds were planted in a fine seedbed of silt loam of intermediate moisture. The seeds were planted at a depth of two inches (5.08 cm). First rainfall (0.2"; 0.51 cm) occurred the day following treatment, the second rain (0.25"; 64 cm) two days after treatment; cumulative rainfall 22 days after treatment was 1.8" (4.57 cm). Observations were made 6 weeks after treatment.

TABLE VII

| Compound | Application Mode | Rate (Kg/Ha) | Percent Inhibition | | | | | | | | | | | | | |
|---|---|---|---|---|---|---|---|---|---|---|---|---|---|---|---|---|
| | | | Field Corn | Sweet Corn | Soybeans | Peanuts | Cotton | Sorghum | Bush Bean | Rape | Foxtail (Spp) | Barnyardgrass | Wild Proso Millet | Smart Weed | Lambs-Quarter | Pigweed |
| Ex. 1 | S.A. | 0.56 | 0 | 0 | 0 | 0 | 0 | 0 | 0 | 0 | 62 | 63 | 63 | 0 | 0 | 0 |
| | | 1.12 | 0 | 0 | 5 | 0 | 13 | 3 | 8 | 0 | 92 | 93 | 83 | 0 | 13 | 0 |
| | | 2.24 | 0 | 7 | 0 | 8 | 20 | 17 | 20 | 5 | 93 | 93 | 95 | 50 | 40 | — |
| | | 4.48 | 15 | 27 | 13 | 22 | 25 | 77 | 32 | 33 | 98 | 98 | 97 | 90 | 67 | — |
| | P.P.I. | 0.56 | 0 | 0 | 5 | 17 | 13 | 32 | 23 | 0 | 75 | 75 | 23 | 20 | — | 50 |
| | | 1.12 | 0 | 3 | 7 | 13 | 32 | 53 | 10 | 0 | 90 | 93 | 58 | — | — | 85 |
| | | 2.24 | 5 | 27 | 20 | 15 | 37 | 92 | 37 | 15 | 98 | 98 | 80 | 75 | — | 85 |
| | | 4.48 | 32 | 40 | 40 | 28 | 82 | 98 | 43 | 40 | 100 | 100 | 85 | 85 | — | 95 |
| Ex. 2 | S.A. | 0.56 | 0 | 0 | 0 | 0 | 0 | 0 | 0 | 0 | 50 | 50 | 27 | 0 | 0 | 0 |
| | | 1.12 | 0 | 0 | 0 | 0 | 8 | 0 | 0 | 5 | 85 | 87 | 63 | 10 | 7 | 0 |
| | | 2.24 | 0 | 0 | 3 | 5 | 8 | 5 | 5 | 0 | 90 | 90 | 75 | 20 | 20 | — |
| | | 4.48 | 10 | 23 | 10 | 20 | 43 | 33 | 33 | 30 | 97 | 97 | 93 | 63 | 62 | — |
| | P.P.I. | 0.56 | 0 | 0 | 3 | 0 | 10 | 7 | 5 | 0 | 77 | 85 | 35 | — | — | 33 |
| | | 1.12 | 0 | 0 | 0 | 5 | 23 | 27 | 13 | 15 | 78 | 88 | 48 | 75 | — | 85 |
| | | 2.24 | 0 | 13 | 13 | 17 | 30 | 38 | 22 | 27 | 87 | 95 | 68 | 95 | 95 | 85 |
| | | 4.48 | 13 | 35 | 28 | 45 | 75 | 90 | 63 | 35 | 100 | 100 | 87 | — | 100 | 88 |

The data in Table VII show that, in general, the compound of Examples 1 and 2 performed better as a selective herbicide in the surface application mode than when incorporated in the soil. In more particular, in the surface application tests the herbicide selectively controlled the three weeds in the test at application rates above 0.58 kg/ha (0.5 lb/A) while maintaining crop safety (i.e., up to about 15% maximum injury) in field corn and soybeans up to 4.48 kg/ha (4.0 lb/A) and safety in sweet corn, peanuts, and rape at greater than 2.24 kg/ha (2.0 lb/A) and in cotton, sorghum and bush beans at just under 2.24 kg/ha. In the PPI tests, the compound of Example 1 selectively controlled the foxtail species and barnyardgrass at less than 1.12 kg/ha (1.0 lb/A) while maintaining crop safety in field corn, peanuts and rape at rates up to 2.24 kg/ha and slightly below 2.24 kg/ha for soybeans.

Other test data for the compound of Example 1 established its effectiveness for premergence selective control or suppression in soybeans, corn, cotton, peanuts, dry beans, lima beans. red kiney beans, potatoes, tree fruits, e.g., citrus and pome fruits, and turf grasses, of weeds, including annual grasses such as barnyard grass, crabgrass, giant foxtail, green foxtail, robust purple foxtail, robust white foxtail, yellow foxtail, goosegrass, fall panicum, red rice, broadleaf signal grass and witchgrass, and annual broadleafs such as carpetweed, black nightshade, hairy nightshade, pigweed, purslane and Florida pusley and perennials such as quackgrass, yellow and purple nutsedges. In addition, the compound of Example 1 reduces competition from seedling johnsongrass, Texas panicum, sandbur, shattercane, Florida beggarweed, lambsquarters, ragweed, prickley sida and smartweed. The compound of Example 1 is generally useful in crops, non-crops and industrial applications.

It will be understood by those skilled in the art that not all of the named weeds are selectively controlled in all of the named crops under all conditions of climate, soil, moisture and/or herbicide application modes. Selectivity data for control of the foregoing weeds in the crops soybeans, corn, cotton and peanuts from a plurality of field tests in various locations under various conditions of soil, moisture, etc., is shown collectively in Tables VIII–XI, respectively. In the tables "WAT" means "Weeks After Treatment" of the plants with the herbicide, applied either by surface application ("S.A.") or by preplant incorporation ("PPI") in the soil; application rate data for each crop/weed combination is shown in terms of $GR_{15}$ and $GR_{85}$ rates (defined above); the $GR_{15}/GR_{85}$ ratio resulting in the selectivity factor, "S.F."; "NS" indicates non-selective and a dash (—) indicates marginal or indeterminate selectivity, e.g., because actual $GR_{15}$ and $GR_{85}$ rates were higher or lower than maximum or minimum rates used in the indicated test). In Tables VIII–XI, a blank indicates that the plant species was not in a particular test plot or that the data was not obtained or was less significant than other data presented, e.g., some 3 WAT observations are omitted in favor of 6 WAT data or 6 WAT data omitted because the 3 WAT data was definitive.

TABLE VIII

| Compound | Crop/Weed Combination | Appln. Mode | WAT | $GR_{15}/GR_{85}$ | S.F. |
|---|---|---|---|---|---|
| Ex. 1 | Soybeans/Giant foxtail | S.A. | 3 | >4.5/<1.1 | (>4) |
| | | | 5 | | |
| | | P.P.I. | 3 | >4.5/<1.1 | (>4) |
| | | | 5 | >4.5/<1.1 | (>4) |
| | | | 8 | | |
| | Soybeans/Yellow foxtail | S.A. | 6 | 2.5/1.1 | (2) |
| | | P.P.I. | 6 | 1.4/<1.12 | (>1) |
| | Soybeans/Lambsquarters | S.A. | 6 | 2.5/2.5 | (1) |
| | | P.P.I. | 6 | 1.4/2.8 | (NS) |
| | Soybeans/Pennsylvania Smartweed | P.P.I. | 8 | 4.5/2.5 | (2) |

The data in Table VIII show that the compound of Example 1 selectively controlled or suppressed giant and yellow foxtails, lambsquarters and Pennsylvania smartweed in soybeans from 6–8 WAT by either the S.A. or P.P.I. modes of application.

TABLE IX

| Compound | Crop/Weed Combination | Appln. Mode | WAT | $GR_{15}/GR_{85}$ | S.F. |
|---|---|---|---|---|---|
| Ex. 1 | Corn/Giant foxtail | S.A. | 6 | 4.5/<1.1 | (4) |
| | | S.A. | 6.5 | >7.8/8.4 | (NS) |
| | | P.P.I. | 6 | 4.8/2.0 | (2.5) |
| | | P.P.I. | 6.5 | >6.7/4.5 | (1.5) |
| | Corn/Morningglory | S.A. | 3 | >4.5/>4.5 | (—) |
| | | S.A. | 6 | >4.5/>4.5 | (—) |
| | | P.P.I. | 3 | 4.8/>4.5 | (—) |
| | | P.P.I. | 6 | 4.8/>4.5 | (—) |
| | Corn/Cocklebur | S.A. | 3 | >4.5/>4.5 | (—) |
| | | S.A. | 6 | >4.5/>4.5 | (—) |
| | | P.P.I. | 3 | 4.8/>4.5 | (—) |
| | | P.P.I. | 6 | 4.8/>4.5 | (—) |

The data in Table IX show that the compound of Example 1 selectively controlled giant foxtail in corn from 6–6.5 WAT by either the S.A. or P.P.I. mode of application; selectively of morninggglory and cocklebur was undetermined at test rates, but suppression of these weeds was exhibited.

TABLE X

| Compound | Crop/Weed Combination | Appln. Mode | WAT | $GR_{15}/GR_{85}$ | S.F. |
|---|---|---|---|---|---|
| Ex. 1 | Cotton/Purple nutsedge | S.A. | 6 | 3.6/1.7 | (2) |
| | | S.A. | 9 | 3.4/2.2 | (1.5) |
| | | P.P.I. | 6 | 3.4/4.2 | (NS) |
| | Cotton/Prickly sida | S.A. | 6 | 3.6/3.1 | (1) |
| | | S.A. | 9 | 3.4/4.8 | (NS) |
| | | P.P.I. | 6 | 3.4/4.8 | (NS) |
| | Cotton/Purslane | S.A. | 9 | 3.4/2.0 | (1.5) |
| | Cotton/Crabgrass (smooth and hairy) | S.A. | 7 | 1.4/<1.1 | (>1) |
| | | P.P.I. | 7 | 0.84/1.1 | (NS) |
| | Cotton/Goosegrass | P.P.I. | 7 | 0.84/<1.1 | (—) |

The data in Table X show that the compound of Example 1 selectively controlled purple nutsedge and purslane up to 9 WAT, prickly sida up to 6 WAT and crabgrass up to 7 WAT; control of goosegrass was marginal or indeterminate.

In Table XI is presented preemergence activity data for the compound of Example 1 against three resistant annual weeds, i.e., Texas panicum, bristly starbur and Florida pusley in peanuts for periods up to 12 WAT. The data in Table XI represent the average of three replicate runs in sandy loam soil having 1.3% organic matter, 79.2% sand and 10% clay; herbicide surface applied.

TABLE XI

| | | Percent Inhibition | | | | | | | | | | |
|---|---|---|---|---|---|---|---|---|---|---|---|---|
| | | Peanuts WAT | | | Texas Panicum WAT | | | Bristly Starbur WAT | | | Florida Pusley WAT | | |
| Compound | Rate (Kg/Ha) | 4 | 8 | 12 | 4 | 8 | 12 | 4 | 8 | 12 | 4 | 8 | 12 |
| Ex. 1 | 2.24 | 5 | 0 | 0 | 50 | 67 | 40 | | 78 | 40 | 0 | 90 | |
| | 3.36 | 10 | 0 | 0 | 68 | 63 | 55 | | 85 | 60 | 0 | | |
| | 4.48 | 17 | 7 | 0 | 85 | 88 | 78 | | 95 | 100 | 0 | 95 | 95 |

Reference to the data in Table XI shows that the compound of Example 1 selectively controlled Texas panicum in peanuts for up to 8 weeks and provided a large degree of control even at 12 WAT with about 4.48 kg/ha (4.0 lb/A); selective control of bristly starbur was achieved at 3.36 kg/ha (3.0 lb/A) for 8 weeks and complete control maintained for 12 WAT at 4.48 kg/ha (4.0 lb/A) and selective control of Florida pusley was achieved with less than 2.24 kg/ha at 8 WAT and with 4.48 kg/ha 95% control was attained at 12 WAT.

In other greenhouse tests, compounds according to this invention have shown selective control of a variety of annual and perennial weeds in various crops. As further illustrative, the compound of Example 1 selectively controlled purple nutsedge in both corn nd soybeans, the respective crop/weed $GR_{15}/GR_{85}$ ratios (expressed in kg/ha) being 0.67/0.25 (S.F.=2.7) in corn and 1.1/0.25 (S.F.=4.5) in soybeans. The compound of Example 8 has shown selective control of yellow nutsedge and quackgrass in corn and soybeans. The respective crop/yellownutsedge $GR_{15}/GR_{85}$ ratios being >2.2/0.95 (S.F.=2.5) in corn; 2.2/0.5 (SF=4.5) in soybeans and the respective $GR_{15}/GR_{85}$ ratios for both corn and soybeans in quackgrass being >2.2/0.5 (S.F.=4.5). In a test against yellow nutsedge in cotton, the $GR_{15}/GR_{85}$ ratio (average of two replicates) was 2.0/0.95 (S.F.=2). Similarly, the compound of Example 9 exhibited selective control of yellow nutsedge in cotton, the $GR_{15}/GR_{85}$ ratio being 0.7/0.47 (S.F.=1.5).

In one multi-crop test in the greenhouse, the compounds of Examples 1, 9, and 10 were tested against yellow nutsedge in cotton, soybeans, corn and rice; each compound was non-selective with respect to yellow nutsedge in rice. However, markedly high selectivities for yellow nutsedge in cotton, soybeans and corn were shown for each of the compounds in the test; the respective $GR_{15}$ and $GR_{85}$ rates for these compounds are shown in Table XII selectivity factors are shown in parenthesis after each crop.

TABLE XII

| Compound | $GR_{85}$ (Kg/Ha) Yellow Nutsedge | Cotton | $GR_{15}$ (Kg/Ha) Soybeans | Corn |
|---|---|---|---|---|
| Ex. 1 | 0.24 | 2.0 (8) | 0.87 (3.6) | 0.69 (2.9) |
| Ex. 9 | 0.21 | 2.5 (12) | 2.0 (9.5) | 2.5 (12) |
| Ex. 10 | 0.38 | 2.8 (7.4) | 2.2 (5.8) | 1.7 (4.5) |

The compounds of Examples 1 and 9–10 were further tested against quackgrass in wheat, soybeans and corn; each compound was found to be non-selective in wheat. The selectivity data for the above compounds agaist quackgrass in soybeans and corn is shown in Table XIII.

TABLE XIII

| Compound | $GR_{85}$ (Kg/Ha) Quackgrass | $GR_{15}$ (Kg/Ha) Soybeans | Corn |
|---|---|---|---|
| Ex. 1 | 0.07 | 0.81 (11.6) | 0.69 (10) |
| Ex. 9 | 0.36 | 1.7 (4.7) | 1.7 (4.7) |
| Ex. 10 | 0.45 | 1.5 (3.3) | 2.5 (5.6) |

In yet other greenhouse tests of herbicidal efficacy, the compounds of Examples 1 and 2 were tested against a number of annual grasses including resistant weeds such as Texas panicum, seedling johnsongrass, shattercane, alexandergrass, wild proso millet (panicum milicaeum), red rice and itchgrass. The results of these tests are shown in Table XIV; selectivity factors are noted in parenthesis; a dash indicating marginal or undetermined selectivity.

TABLE XIV

| Compound | $GR_{15}$ Rate (Kg/Ha) Soybeans | $GR_{85}$ Rate (Kg/Ha) | | | | | | | |
|---|---|---|---|---|---|---|---|---|---|
| | | Texas Panicum | S. Johnsongrass | Shattercane | Alexandergrass | Wild Proso millet | Fall Panicum | Red Rice | Itchgrass |
| Ex. 1 | >1.1 | 1.1 (>1.0) | 0.14 (>8.0) | 0.28 (>4.0) | 0.56 (>2.0) | 1.1 (>1.0) | <0.07 (>16) | 0.2 (>5.5) | 1.1 (>1.0) |
| Ex. 2 | >1.1 | >1.12 (—) | 0.28 (>4.0) | 0.93 (>1.12) | >1.1 (—) | 1.1 (>1.0) | <0.07 (>16) | 0.14 (>8.0) | >1.1 (—) |

The data in Table XIV indicate that the compound of Example 1 selectively controlled every annual weed in the test in soybeans. The compound of Example 2 exhibited positive selective control against all weeds, except Texas panicum, alexandergrass and itchgrass at the maximum test rate of 1.1 kg/ha; a higher rate would have been required to determine selectivity of the compound against the three weeds not exhibiting selective control at the test rate.

In another greenhouse test, the compounds of Examples 3–5, 9 and 10 were tested for their herbicidal efficacy against a variety of resistant annual and perennial weeds in rape. The weeds in this test are generally resistant to acetamide herbicides, hence, selectivity factors would be expected to be relatively low. The data from this test is shown in Table XV.

TABLE XV

| Compound | $GR_{15}$ Rate (Kg/Ha) Rape | $GR_{85}$ Rate (Kg/Ha) | | | | | |
|---|---|---|---|---|---|---|---|
| | | Redroot Pigweed | Common Purslane | Common Ragweed | Purple Nutsedge | Alexandergrass | Prickly Sida |
| Ex. 3 | 0.90 | 0.39 (2.3) | 0.70 (1.3) | 0.49 (1.8) | 0.12 (7.5) | 0.14 (6.3) | >1.12 (NS) |
| Ex. 4 | >1.12 | 0.50 (>2.2) | >1.12 (—) | 1.03 (>1.1) | 0.25 (>4.5) | 0.42 (>2.7) | >1.12 (—) |
| Ex. 5 | >1.12 | 0.50 (>2.2) | >1.12 (—) | 0.98 (>1.1) | 0.23 (>4.9) | 0.7 (>1.6) | >1.12 (—) |
| Ex. 9 | 0.98 | 0.70 (1.4) | 0.78 (1.3) | >1.12 (NS) | 0.19 (5.2) | 0.19 (5.2) | >1.12 (NS) |
| Ex. 10 | >1.12 | 0.70 (>1.6) | >1.12 (—) | >1.12 (—) | 0.18 (>6.2) | 0.36 (>3.1) | >1.12 (—) |

Referring to the data in Table XV, it will be seen that all of the invention compounds exhibited selectivity in rape against redroot pigweed, purple nutsedge and alexandergrass. Example 3 selectively controlled all weeds in the test; Example 9 selectively controlled all weeds, except prickly sida and common ragweed; Examples 4 and 5 selectively controlled all weeds except common purslane and prickly sida and Example 10 selectively controlled all weeds, except common purslane, prickly sida and common ragweed. It is pointed out that the maximum test rate in Table XV is 1.12 kg/ha, hence in each instance where the selectivity of a weed was indicated as indeterminate, positive selectivity maybe achieved at a higher rate.

Additional greenhouse tests were made to test certain compounds of this invention against a plurality of problem weeds in peanuts and lima beans; except for fall panicum, the test weeds are particularly resistant weeds; the test data is set forth in Table XVI.

against itchgrass in lima beans and the compound of Example 10 against Texas panicum in peanuts, the invention compounds exhibited positive selective control of each weed in the test in lima beans and peanuts. Although in several instances the margin of selectivity was not large, it is again pointed out that all but one of the weeds in the test are resistant weeds and the maximum test rate was only 1.0 lb/A (1.12 kg/ha), thus indicating the excellent herbicidal efficacy of the invention compounds.

TABLE XVI

| Compound | $GR_{15}$ Rate (Kg/Ha) | | $GR_{85}$ Rate (Kg/Ha) | | | | | | | | | | | | | |
|---|---|---|---|---|---|---|---|---|---|---|---|---|---|---|---|---|
| | Lima Beans | Peanuts | Seedling Johnson Grass | | Texas Panicum | | Wild Proso Millet | | Red Rice | | Itchgrass | | Fall Panicum | | Shattercane | |
| Ex. 3 | 0.49 | >1.12 | 0.23 | (2.1) | 0.43 | (1.1) | 0.27 | (1.8) | 0.37 | (1.3) | 0.51 | (NS) | 0.08 | (6) | 0.11 | (4.5) |
| | | | 0.23 | (>4.9) | 0.43 | (>2.6) | 0.27 | (>4.2) | 0.37 | (>3) | 0.51 | (>2.2) | 0.08 | (>14) | 0.11 | (>10.2) |
| Ex. 4 | >1.12 | 0.98 | 0.51 | (>2.2) | 0.56 | (>2) | 0.47 | (>2.4) | 0.42 | (>2.7) | 0.50 | (>2.2) | 0.13 | (>8.6) | 0.51 | (>2.2) |
| | | | 0.51 | (1.9) | 0.56 | (1.8) | 0.47 | (2.1) | 0.42 | (2.3) | 0.50 | (2) | 0.13 | (7.5) | 0.51 | (1.9) |
| Ex. 5 | >1.12 | 0.56 | 0.37 | (>3) | 0.53 | (>2.1) | 0.56 | (>2) | 0.53 | (>2.1) | 0.56 | (>2) | 0.28 | (>4) | 0.56 | (>2) |
| | | | 0.37 | (1.5) | 0.53 | (1.1) | 0.56 | (1) | 0.53 | (1.1) | 0.56 | (1) | 0.28 | (2) | 0.56 | (1) |
| Ex. 9 | 0.75 | 0.90 | 0.25 | (3) | 0.56 | (1.3) | 0.56 | (1.3) | 0.42 | (1.8) | 0.53 | (1.4) | 0.13 | (5.8) | 0.21 | (3.6) |
| | | | 0.25 | (3.6) | 0.56 | (1.6) | 0.56 | (1.6) | 0.42 | (2.1) | 0.53 | (1.7) | 0.13 | (6.9) | 0.21 | (4.3) |
| Ex. 10 | >1.12 | 0.98 | 0.36 | (>3.1) | 1.1 | (>1) | 0.80 | (>1.4) | 0.98 | (>1.1) | 0.90 | (>1.2) | 0.22 | (>5.1) | 0.56 | (>2) |
| | | | 0.36 | (2.7) | 1.1 | (NS) | 0.80 | (1.2) | 0.98 | (1) | 0.90 | (1.1) | 0.22 | (4.5) | 0.56 | (1.8) |

In Table XVI, the selectivity factors for the test compounds for each weed in lima beans is shown as the first or upper value in parenthesis and the selectivity factors for each weed in peanuts is shown as the second or lower value in parenthesis for each compound. For example, the selectivity factor for the compound of Example 3 for seedling johnsongrass in lima beans is 2.1 and in peanuts, >4.9; the selectivity factor for Texas panicum in lima beans is 1.1 and in peanuts, >2.6, etc.

It will be noted from the data in Table XVI, that, but for the two exceptions of the compound of Example 3

A distinct advantage of a herbicide is its ability to function in a wide variety of soil types. Accordingly, data is presented in Tables XVII A–XVII C, respectively, showing the herbicidal effect of the compounds of Examples 1–5 and 9 on quackgrass in soybeans in a wide variety of soil types of varying organic matter and clay content. The herbicide treatments were by soil incorporation with seeds planted 0.375 in (0.95 cm) deep, with 0.25 in (0.64 cm overhead irrigation. Observations were made about three weeks after treatment. Selectivity factors are shown in parenthesis.

TABLE XVII A

| | | | Ex. 1 | | Ex. 2 | |
|---|---|---|---|---|---|---|
| | Organic Matter | | $GR_{15}$ | $GR_{85}$ (Kg/Ha) | $GR_{15}$ | $GR_{85}$ (Kg/Ha) |
| Soil Type | % | Clay % | Soybeans | Quackgrass | Soybeans | Quackgrass |
| Ray silt loam | 1.0 | 9.6 | 1.1 | 0.22 (5) | 2.2 | 0.28 (8) |
| Sarpy silty clay | 2.3 | 30–35 | >2.2 | 0.28 (>8) | >2.2 | 0.43 (>5) |
| Wabash silty clay | 4.3 | 33.0 | — | 0.28 (—) | — | 0.34 (—) |
| Drummer silty clay | 6.0 | 37.0 | >2.2 | 0.11 (20) | >2.2 | 0.56 (>4) |
| Florida sand | 6.8 | 1.8 | 2.0 | 0.2 (10) | 1.7 | 0.22 (7.5) |
| Florida muck | 60 | — | >2.2 | 0.52 (>4.5) | >2.2 | 0.95 (>2) |

TABLE XVII B

| | Organic Matter | | $GR_{15}$ | $GR_{85}$ (Kg/Ha) | $GR_{15}$ | $GR_{85}$ (Kg/Ha) |
|---|---|---|---|---|---|---|
| Soil Type | % | Clay % | Soybeans | Quackgrass | Soybeans | Quackgrass |
| | | | | Ex. 1 | | Ex. 3 |
| Ray silt loam | 1.0 | 9.6 | 2.2 | 0.13 (16.5) | — | — |
| Sarpy silty clay | 2.3 | 30–35 | 2.2 | 0.10 (22) | — | — |
| Wabash silty clay | 4.3 | 33.0 | 2.2 | 0.13 (17) | 2.0 | 0.22 (9) |
| Drummer silty clay | 6.0 | 37.0 | 2.2 | 0.17 (13) | — | — |
| Florida sand | 6.8 | 1.8 | 2.2 | 0.48 (4.5) | 2.0 | 0.72 (2.5) |
| Florida muck | 60 | — | 2.2 | 0.78 (>3) | >2.2 | 1.1 (>2) |
| | | | | Ex. 4 | | Ex. 5 |
| Ray silt loam | 1.0 | 9.6 | 3.0 | 0.13 (23) | 2.0 | >2.2 (NS) |
| Sarpy silty clay | 2.3 | 30–35 | 2.2 | 0.39 (5.5) | 3.0 | 1.6 (2) |
| Wabash silty clay | 4.3 | 33.0 | 3.0 | 0.24 (12.5) | 2.2 | 1.6 (1.5) |
| Drummer silty clay | 6.0 | 37.0 | 2.2 | 0.11 (20) | 2.2 | 1.1 (2) |
| Florida sand | 6.8 | 1.8 | 2.2 | 0.25 (9) | 3.0 | 1.1 (3) |
| Florida muck | 60 | — | >2.2 | 0.67 (>3) | >2.0 | 3.0 (—) |

TABLE XVII C

| | Organic Matter | | Ex. 1 | | Ex. 9 | |
| | | | $GR_{15}$ | $GR_{85}$ (Kg/Ha) | $GR_{15}$ | $GR_{85}$ (Kg/Ha) |
| Soil Type | % | Clay % | Soybeans | Quackgrass | Soybeans | Quackgrass |
|---|---|---|---|---|---|---|
| Ray silt loam | 1.0 | 9.6 | 2.0 | 0.10 (19.5) | >2.2 | 0.13 (>16.5) |
| Sarpy silty clay | 2.3 | 30–35 | >2.2 | 0.13 (>16.5) | >2.2 | 0.13 (>16.5) |
| Wabash silty clay | 4.3 | 33.0 | 2.2 | 0.07 (31.5) | 3.0 | 0.24 (12.5) |
| Drummer silty clay | 6.0 | 37.0 | 2.0 | 0.13 (14.5) | >2.2 | 0.17 (>13) |
| Florida muck | 60 | — | >2.2 | 0.74 (>3) | >2.2 | 0.73 (>3) |

The data in Tables XVII A–C show that the compounds of Examples 1–5 and 9 appear to be quite insensitive to soil types of varying organic matter content, exhibiting selective control of quackgrass in soybeans in soils ranging from 1.0% to 60% organic matter and clay content from at least 1.8% to about 37%. The data on soybeans in Wabash silty clay in Table XVIIA was indeterminate in this test. Also, the indicated selectivity factors in sarpy and Drummer silty clay and Florida muck are minimum values, since the maximum test rate was 2.2 kg/ha and the herbicide was safe on soybeans at some rate above 2.2 kg/ha; similar comments apply to the data in Tables XVII B and C.

Laboratory tests were conducted to determine the resistance of herbicides according to this invention to leaching into the soil and resulting herbicidal efficacy. In these tests, the compounds of Examples 1, 3–5 and 10 were formulated in acetone and then sprayed at different concentrations onto a weighed amount of Ray silt loam and Drummer silty clay loam contained in pots having filter paper covering drainage holes in the pot bottoms. The pots containing the treated soil were subjected to leaching by placing on a turntable which rotated under two nozzle tips of a water container calibrated to deliver one inch (2.5 cm) of water per hour simulating rainfall. Leaching rates were adjusted by varying the amount of time on the turntable. Water was delivered to the soil in the pots and allowed to percolate through the filter paper and drainage holes. The pots were then allowed to sit for three days at ambient room temperature. The treated soil in the pots was then removed, crumbled and placed as a surface layer on top of other pots containing the above soils seeded with barnyardgrass seeds. The pots were then placed on greenhouse benches, sub-irrigated and allowed to grow for 2–3 weeks. Visual ratings of percent growth inhibition compared to control (untreated) pots and fresh weights for barnyardgrass were recorded; the data from the control represents six replications and that for the test compounds three replications; test data are shown in Table XVIII. Fresh weights of the weed were not measured for the tests in Drummer silty clay loam soil, or for the compound of Example 10.

TABLE XVIII

| | | | Barnyardgrass | | | |
| | | | Percent Inhibition | | Fresh Weight (Grams) | |
| Compound | Rate (Kg/Ha) | Rain (Cm) | Ray Silt Loam | Drummer Silt Clay | Ray Silt Loam | Drummer Silt Clay |
|---|---|---|---|---|---|---|
| Control | 0 | 0 | | | 4.37 | |
| | 0 | 1.27 | | | 3.88 | |
| | 0 | 5.08 | | | 4.14 | |
| | 0 | 10.16 | | | 3.98 | |
| | | | | | Avg. 4.10 | |
| Ex. 1 | 2.2 | 0 | 100 | 100 | 0 | — |
| | | 1.27 | 100 | 100 | 0 | — |
| | | 5.08 | 95 | 100 | 0.20 | — |
| | | 10.16 | 35 | 100 | 2.65 | — |
| | 0.56 | 0 | 100 | 100 | 0 | — |
| | | 1.27 | 100 | 100 | 0 | — |
| | | 5.08 | 70 | 100 | 1.21 | — |
| | | 10.16 | 33 | 100 | 2.73 | — |
| | 0.14 | 0 | 95 | 100 | 0.20 | — |
| | | 1.27 | 96 | 97 | 0.17 | — |
| | | 5.08 | 58 | 95 | 1.74 | — |
| | | 10.16 | 20 | 20 | 3.26 | — |
| Ex. 3 | 2.36 | 0 | 100 | 100 | 0 | — |
| | | 1.27 | 100 | 100 | 0 | — |
| | | 5.08 | 100 | 100 | 0 | — |
| | | 10.16 | 95 | 100 | 0.22 | — |
| | 0.56 | 0 | 100 | 100 | 0 | — |
| | | 1.27 | 100 | 100 | 0 | — |
| | | 5.08 | 94 | 100 | 0.24 | — |
| | | 10.16 | 52 | 100 | 1.97 | — |
| | 0.14 | 0 | 99 | 81 | 0.05 | — |
| | | 1.27 | 95 | 99 | 0.22 | — |
| | | 5.08 | 63 | 94 | 1.53 | — |
| | | 10.16 | 14 | 54 | 3.51 | — |
| Ex. 4 | 2.2 | 0 | 100 | 100 | 0 | — |
| | | 1.27 | 100 | 100 | 0 | — |
| | | 5.08 | 92 | 100 | 0.31 | — |
| | | 10.16 | 71 | 100 | 1.18 | — |
| | 0.56 | 0 | 99 | 100 | 0.02 | — |
| | | 1.27 | 100 | 100 | 0 | — |
| | | 5.08 | 89 | 100 | 0.44 | — |

TABLE XVIII-continued

| | | | Barnyardgrass | | | |
|---|---|---|---|---|---|---|
| | | | Percent Inhibition | | Fresh Weight (Grams) | |
| Compound | Rate (Kg/Ha) | (Cm) | Ray Silt Loam | Rain Drummer Silt Clay | Ray Silt Loam | Drummer Silt Clay |
| | | 10.16 | 17 | 96 | 3.41 | — |
| | 0.14 | 0 | 98 | 70 | 0.01 | — |
| | | 1.27 | 90 | 96 | 0.41 | — |
| | | 5.08 | 38 | 85 | 2.77 | — |
| | | 10.61 | 12 | 47 | 3.62 | — |
| Ex. 5 | 2.2 | 0 | 100 | 100 | 0 | — |
| | | 1.27 | 100 | 100 | 0 | — |
| | | 5.08 | 99 | 100 | 0.03 | — |
| | | 10.16 | 84 | 100 | 0.64 | — |
| | 0.56 | 0 | 99 | 50 | 0.04 | — |
| | | 1.27 | 99 | 100 | 0.02 | — |
| | | 5.08 | 90 | 93 | 0.41 | — |
| | | 10.16 | 72 | 84 | 1.17 | — |
| | 0.14 | 0 | 84 | 12 | 0.66 | — |
| | | 1.27 | 90 | 26 | 0.43 | — |
| | | 5.08 | 58 | 20 | 1.72 | — |
| | | 10.16 | 29 | 12 | 2.92 | — |
| Ex. 10 | 2.2 | 0 | 100 | 100 | — | — |
| | | 1.27 | 100 | 100 | — | — |
| | | 5.08 | 100 | 99 | — | — |
| | | 10.16 | 98 | 98 | — | — |
| | 0.56 | 0 | 100 | 99 | — | — |
| | | 1.27 | 100 | 98 | — | — |
| | | 5.08 | 100 | 98 | — | — |
| | | 10.16 | 90 | 98 | — | — |
| | 0.14 | 0 | 100 | 90 | — | — |
| | | 1.27 | 100 | 85 | — | — |
| | | 5.08 | 98 | 80 | — | — |
| | | 10.16 | 65 | 70 | — | — |

Reference to the data in Table XVIII indicate that the compounds of this invention are quite resistant to leaching into the soil under varying conditions of rainfall. In particular, at the 2.2 kg/ha (2.0 lb/A) rate of application, each of the invention compounds controlled barnyardgrass under the equivalent of 10.16 cm (4.0 inches) of rainfall in Ray silt loam and Drummer silt clay loam soil except the compounds of Examples 2 and 4 in Ray silt wherein control was maintained under the equivalent of 5.08 cm (2.0 inches) of rainfall. Even at the low application rate of 0.14 kg/ha (0.125 lb/A), the compounds of Examples 2, 3 and 4 controlled barnyardgrass in Drummer silty clay loam under the equivalent of 5.08 cm rainfall and Example 10 was close to such control.

Toxicology studies on the compound of Example 1 have indicated the compound to be quite safe. It is slightly toxic (OLD$_{50}$ 2300 mg/kg; MLD$_{50}$ >5010 mg/kg) and has slight eye irritation and no skin irritation. No special handling procedures beyond normal precautions are deemed necessary.

Therefore, it will be appreciated from the foregoing detailed description that compounds according to this invention have demonstrated unexpected and outstandingly superior herbicidal properties both absolutely and relative to the most structurally-relevant compounds of the prior art.

More particularly, the compounds of this invention have proven to be outstanding selective herbicides, particularly in the suppression of hard-to-kill perennial (i.e., quackgrass and yellow nutsedge), as well as annual weeds in soybeans and corn. Individual compounds of the present invention have demonstrated outstanding selective control or suppression of perennial weeds, such as quackgrass and nutsedges, and resistant annual weeds, such as Texas panicum, itchgrass, wild proso millet, alexandergrass, seedling johnsongrass, shattercane and red rice, as well as less-resistant annuals and perennials in crops such as corn, soybeans, cotton, peanuts and snap beans.

The herbicidal compositions of this invention including concentrates which require dilution prior to application contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, granules, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these.

The compositions of this invention, particularly liquids and wettable powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acidesters of hexitol anhydrides (e.g., sorbitan). Preferred dispersants are methyl cellulose, polyvinyl alcohol, sodium lignin sulfonates, polymeric alkyl, naphthalene sulfonates, sodium naphthalene sulfonate, and the polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from about 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.00 parts of the solid inert extender can be replaced by a corrosion inhibitor of anti-foaming agent or both.

Other formulations include concentrates comprising from 0.1 to 60% by weight of the active ingredient on a suitable extender; these dusts may be diluted for application at concentrations within thhe range of from about 0.1–10% by weight.

Aqueous suspensions or emulsions may be prepared by stirring an aqueous mixture of a water-insoluble active ingredient and an emulsification agent until uniform and then homogenized to give stable emulsion of very finely-divided particles. The resulting concentrated aqueous suspension is characterized by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

In another form of aqueous suspensions, a water-immiscible herbicide is encapsulated to form microencapsulated phase dispersed in an aqueous phase. In one embodiment, minute capsules are formed by bringing together an aqueous phase containing a lignin sulfonate emulsifier and a water-immiscible chemical and polymethylene polyphenylisocyanate, dispersing the water-immiscible phase in the aqueous phase followed by addition of a polyfunctional amine. The isocyanate and amine compounds react to form a solid urea shell wall around particles of the water-immiscible chemical, thus forming microcapsules thereof. Generally, the concentration of the microencapsulated material will range from about 480 to 700 g/l of total composition preferably 480 to 600 g/l. The microencapsulation process referred to here is described in more detail in the assignee's U.S. Pat. No. 4,280,833.

Concentrates are usually solutions of active ingredient in water-immiscible or partially water-immiscible solvents together with a surface active agent. Suitable solvents for the active ingredient of this invention include dimethylformide, dimethylsulfoxide, N-methyl-pyrrolidone, hydrocarbons and water-immiscible ethers, esters or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts preferably from about 3 to 20 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention include, for example, triazines, ureas, carbamates, acetamides, acetanilides, uracils, acetic acid or phenol derivatives, thiolcarbamates, triazoles, benzoic acids, nitriles, biphenyl ethers and the like such as, but not limited to:

HETEROCYCLIC NITROGEN/SULFUR DERIVATIVES 2-(4-chloro-6-ethylamino)-s-triazin-2-ylamino)-2-methylpropionitrile
2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-a:2',1'-c)-pyrazidiinium salt
5-Bromo-3-isopropyl-6-methyluracil
1,1'-Dimethyl-4,4'-bipyridinium

UREAS

N'-(4-chlorophenoxy)phenyl-N,N-dimethylurea
N,N-dimethyl-N'-(3-chloro-4-methylphenyl)urea
3-(3,4-dichlorophenyl)-1,1-dimethylurea
1,3-Dimethyl-3-(2-benzothiazolyl)urea
3-(p-Chlorophenyl)-1,1-dimethylurea
1-Butyl-3-(3,4-dichlorophenyl)-1-methylurea

CARBAMATES/THIOLCARBAMATES

2-Chloroallyl diethyldithiocarbamate
S-(4-chlorobenzyl)N,N-diethylthiolcarbamate
Isopropyl N-(3-chlorophenyl)carbamate
S-2,3-dichloroallyl N,N-diisopropylthiolcarbamate
Ethyl N,N-dipropylthiolcarbamate
S-propyl dipropylthiolcarbamate

ACETAMIDES/ACETANILIDES/ANILINES/AMIDES

2-Chloro-N,N-diallylacetamide
N,N-dimethyl-2,2-diphenylacetamide
N-(2,4-dimethyl-5-[[(trifluoromethyl)sulfonyl]amino]phenyl)acetamide
N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
$\alpha,\alpha,\alpha$-Trifluoro-2,6-dinitro-N,N-dipropyl-p-toluidine
N-(1,1-dimethylpropynyl)-3,5-dichlorobenzamide

ACIDS/ESTERS/ALCOHOLS 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl)glycine and its $C_{1-6}$ monoalkyl amine and alkaline metal salts and combinations thereof

ETHERS 2,4-Dichlorophenyl-4-nitrophenyl ether
2-Chloro-$\alpha,\alpha,\alpha$-trifluoro-p-tolyl-3-ethoxy-4-nitrodiphenyl ether

MISCELLANEOUS 2,6-Dichlorobenzonitrile
Monosodium acid methanearsonate Disodium methanearsonate Fertilizers useful in combination with the active ingredients include, for example, ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

I. EMULSIFIABLE CONCENTRATES

| | Weight Percent |
|---|---|
| A. Compound of Example No. 1 | 50.0 |
| Calcium dodecylbenzene sulfonate/polyoxyethylene ethers blend (e.g., Atlox ® 3437F) | 4.85 |
| Calcium dodecylbenzene sulfonate (FloMo 60H) | 0.15 |
| C9 aromatic solvent | 45.00 |
| | 100.00 |
| B. Compound of Example No. 3 | 85.0 |
| Calcium dodecyl sulfonate/alkylaryl polyether alcohol blend | 4.0 |
| C9 aromatic hydrocarbons solvent | 11.0 |
| | 100.00 |
| C. Compound of Example No. 5 | 5.0 |
| Calcium dodecylbenzene sulfonate/polyoxyethylene ethers blend (e.g., Atlox 3437F) | 1.0 |
| Xylene | 94.0 |
| | 100.00 |

II. LIQUID CONCENTRATES

| | Weight Percent |
|---|---|
| A. Compound of Example No. 3 | 10.0 |
| Xylene | 90.0 |
| | 100.00 |
| B. Compound of Example No. 4 | 85.0 |
| Diemthyl sulfoxide | 15.0 |
| | 100.00 |
| C. Compound of Example No. 5 | 50.0 |
| N—methylpyrrolidone | 50.0 |
| | 100.00 |
| D. Compound of Example No. 6 | 5.0 |
| Ethoxylated castor oil | 20.0 |
| Rhodamine B | .5 |
| Diemthyl formamide | 74.5 |
| | 100.00 |

III. EMULSIONS

| | Weight Percent |
|---|---|
| A. Compound of Example No. 9 | 40.0 |
| Polyoxyethylene/polyoxypropylene block with butanol (e.g. Tergitol ® XH) | 4.0 |
| Water | 56.0 |
| | 100.00 |
| B. Compound of Example No. 10 | 5.0 |
| Polyoxyethylene/polyoxypropylene block copolymer with butanol | 3.5 |
| Water | 91.5 |
| | 100.00 |

IV WETTABLE POWDERS

| | Weight Percent |
|---|---|
| A. Compound of Example No. 1 | 65.0 |
| Sodium lignosulfonate | 3.0 |
| Sodium N—methyl-N—oleyl-taurate | 1.0 |
| Amorphous silica (synthetic) | 31.0 |
| | 100.00 |
| B. Compound of Example No. 2 | 25.0 |
| Sodium dioctyl sulfosuccinate | 1.25 |
| Calcium lignosulfonate | 2.75 |
| Amorphous silica (synthetic) | 71.0 |
| | 100.00 |
| C. Compound of Example No. 3 | 10.0 |
| Sodium lignosulfonate | 3.0 |
| Sodium N—methyl-N—oleyl-taurate | 1.0 |
| Kaolinite clay | 86.0 |
| | 100.00 |

V. DUSTS

| | Weight Percent |
|---|---|
| A. Compound of Example No. 7 | 2.0 |
| Attapulgite | 98.0 |
| | 100.00 |
| B. Compound of Example No. 8 | 10.0 |
| Montmorillonite | 90.0 |
| | 100.00 |
| C. Compound of Example No. 9 | 15.0 |
| Bentonite | 85.0 |
| | 100.00 |

-continued

| | Weight Percent |
|---|---|
| D. Compound of Example No. 10 | 1.0 |
| Diatomaceous earth | 99.0 |
| | 100.00 |

VI. GRANULES

| | Weight Percent |
|---|---|
| A. Compound of Example No. 1 | 15.0 |
| Granular attapulgite (20/40 mesh) | 85.0 |
| | 100.00 |
| B. Compound of Example No. 6 | 30.0 |
| Diatomaceous earth (20/40) | 70.0 |
| | 100.00 |
| C. Compound of Example No. 8 | 0.5 |
| Bentonite (20/40) | 99.5 |
| | 100.00 |
| D. Compound of Example No. 9 | 5.0 |
| Pyrophyllite (20/40) | 95.0 |
| | 100.00 |

VII. MICROCAPSULES

| | Weight Percent |
|---|---|
| A. Compound of Example No. 1 encapsulated in polyurea shell wall | 49.2 |
| Sodium lignosulfonate (e.g. Reax 88 ®B) | 0.9 |
| Water | 49.9 |
| | 100.00 |
| B. Compound of Example No. 4 capsulated in polyurea shell wall | 10.0 |
| Potassium lignosulfonate (e.g., Reax ®C-21) | .5 |
| Water | 89.5 |
| | 100.00 |
| C. Compound of Example No. 5 encapsulated in polyurea shell wall | 80.0 |
| Magnesium salt of lignosulfate (Treax, LTM ®) | 2.0 |
| Water | 18.0 |
| | 100.00 |

It is within the purview of this invention to formulate compositions containing compounds according to this invention and antidotal (safener) compounds to lessen the herbicidal effect of the invention compounds on crops which are not particularly tolerant thereof, e.g., wheat, sorghum, rice, etc. As exemplary of such safeners there is mentioned the $\alpha,\alpha$, dihaloacetamides, e.g., $\alpha,\alpha$-dichloroN,N-bis(2-propenyl acetamide, $\alpha,\alpha$-dihaloacetylacetanilides substituted on the anilide ring with halogen, $CF_3$ or $NO_2$ groups, e.g., $\alpha$, $\alpha$-dichloro-2'-nitro-4'-trifluoromethyl acetanilide, $\alpha,\alpha$-dichloro-3-fluoroacetanilide, $\alpha,\alpha$-dichloro-3,6-difluoroacetanilide; 1,4-dioxo-8-azaspiro [4,5] decane, 8-(dichloroacetyl); oxazolidines, e.g., 3-($\alpha,\alpha$-dichloroacetyl)-2,2,5-trimethyl oxazolidine; 3-($\alpha,\alpha$-dichloroacetyl)-2,2-dimethyl oxazolidine; anhydrides, e.g., naphthalic anhydride; nitriles, such as $\alpha$-[(cyanomethoxy)benzene]acetonitrile; and $\alpha$-[(1,3-dioxalan-2-yloxy)benzene]acetonitrile; pyrazinediyl compounds such as formamide, N,N'-[1,1'-1,4-dihydro-1,4-pyrazinediyl)-bis(2,2,2-trichloroethylidene)] bis-; bis-trifluoromethyl-substituted anilines or acetanilides, such as bis-3,5-trifluoromethyl aniline, bis-3,5-trifluoromethyl-$\alpha,\alpha$-dichloroacetanilide; substituted benzotrifluorides, such as 3-nitro-4-ethoxybenzotrifluoride; 4-(tetrahydrofurfuryloxy)-3-nitrobenzotrifluoride; thiazoles, e.g., 2,4-disubstituted-5-thiazolecarboxylic acids and derivatives thereof e.g., benzyl 2-chloro-4-trifluoromethyl-5-thiazole carboxylate; ethyl 2-chloro-4-isopropyl-5-thiazolecarboxylate; ethyl 2-chloro-4-trifluoromethyl-5-thiazolecarboxylate; butyl 2-chloro-4-trifluoromethyl-5-thiazolecarboxylate; and the like, as described in U.S. Pat. No. 4,199,506 and in copending U.S. application Ser. Nos. 256,326 and 256,335, filed Apr. 22, 1981, assigned to the assignee herein; optionally-substituted (e.g., with halogen, esp. chlorine) diphenylmethoxy acetic acid and thioacetic acids, esters, salts and amides, e.g., acetic acid, (diphenylmethoxy), phenylmethyl ester, acetic acid, (diphenylmethoxy), propyl ester, acetic acid, (diphenylmethoxy),-2,2,2 trifluoroethyl ester, acetic acid {phenyl (3-(trifluoromethyl)phenyl]methoxy}, 2-methyl-2-propanamine salt and the like, and isoxazoles, e.g., ethyl-5-(4-chlorophenyl)-4-isoxazolecarboxylate; ethyl-5-(2,4-dichlorophenyl)-4-isoxazolecarboxylate; ethyl-5-(4-trifluoromethylphenyl)-4-isoxazolecarboxylate; and the like and described in U.S. Pat. No. 4,243,406.

Safeners, or antidotes, for herbicides may be applied to the crop seed (seed treatment) or by broadcast or in-furrow application, alone or, preferably, in admixture with a carrier by conventional means.

When operating in accordance with the present invention, effective amounts of the acetanilides of this invention are applied to the soil containing the plants, or are incorporated into aquatic media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds of this invention to the locus of undesired weeds is essential and critical for the practice of the present invention. The exact amount of active ingredient to be employed is dependent upon various factors, including the plant species and stage of development thereof, the type and condition of soil, the amount of rainfall and the specific acetanilide employed. In selective pre-emergence application to the plants or to the soil a dosage of from 0.02 to about 11.2 kg/ha, preferably from about 0.04 to about 5.60 kg/ha, or suitably from 1.12 to 5.6 kg/ha of acetanilide is usually employed. Lower or higher rates may be required in some instances. One skilled in the art can readily determine the optimum rate to be applied in any particular case.

The term "soil" is employed in its broadest sense to be inclusive of all conventional "soils" as defined in Webster's New International Dictionary, Second Edition, Unabridged (1961). Thus, the term refers to any substance or media in which vegetation may take root and grow, and includes not only earth but also compost, manure, muck, humus, sand and the like, adapted to support plant growth.

Although the invention is described with respect to specific modifications, the details thereof are not to be construed as limitations except to the extent indicated in the following claims.

I claim:

1. The compound N-(ethoxymethyl)-2'-trifluoromethyl-6'-methyl-2-chloroacetanilide having the formula

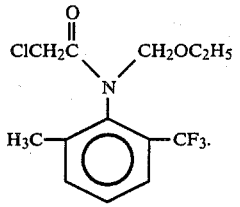

2. Herbicidal composition comprising an adjuvant and a herbicidally effective amount of the compound N-(ethoxymethyl)-2'-trifluoromethyl-6'-methyl-2-chloroacetanilide having the formula

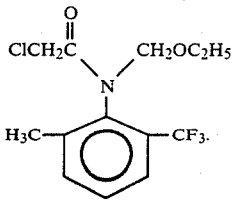

3. Method for combatting undesirable plants in corn which comprises applying to the locus thereof a herbicidally effective amount of N-(ethoxymethyl)-2'-trifluoromethyl-6'-methyl-2-chloroacetanilide.

4. Method for combatting undesirable plants in soybeans which comprises applying to the locus thereof a herbicidally effective amount of N-(ethoxymethyl)-2'-trifluoromethyl-6'-methyl-2-chloroacetanilide.

* * * * *

UNITED STATES PATENT AND TRADEMARK OFFICE
CERTIFICATE OF CORRECTION

PATENT NO. : 4,731,109

DATED : March 15, 1988

INVENTOR(S) : John P. Chupp

It is certified that error appears in the above-identified patent and that said Letters Patent is hereby corrected as shown below:

Column 8, line 22, the word "eater" should be --water--.

Column 19, Table XVI, under "Peanuts", the numbers should be dropped one line each, as follows:

| --Compound | Lima Beans | Peanuts |
|---|---|---|
| Ex. 3 | 0.49 | |
| | | 1.12 |
| Ex. 4 | 1.12 | |
| | | 0.98 |
| Ex. 5 | 1.12 | |
| | | 0.56 |
| Ex. 9 | 0.75 | |
| | | 0.90 |
| Ex. 10 | 1.12 | |
| | | 0.98 -- |

UNITED STATES PATENT AND TRADEMARK OFFICE
CERTIFICATE OF CORRECTION

PATENT NO. : 4,731,109

DATED : March 15, 1988

INVENTOR(S) : John P. Chupp

It is certified that error appears in the above-identified patent and that said Letters Patent is hereby corrected as shown below:

Columns 21, 22, 23 and 24, Table XVIII part of the heading is wrong. The word "Rain" should be over the word "(Cm)", not over the word "Clay".

Signed and Sealed this

Thirteenth Day of June, 1989

*Attest:*

DONALD J. QUIGG

*Attesting Officer*  *Commissioner of Patents and Trademarks*